United States Patent [19]

Horikoshi et al.

[11] Patent Number: 4,962,055

[45] Date of Patent: Oct. 9, 1990

[54] PLASMID, METHOD FOR CONSTRUCTION OF THE SAME, MICROORGANISMS CARRYING THE PLASMID AND METHOD FOR CULTIVATION OF THE MICROORGANISM

[75] Inventors: Koki Horikoshi; Toshiaki Kudo, both of Tokyo; Chiaki Kato, Ohmiya, all of Japan

[73] Assignee: Rikagaku Kenkyusho, Wako, Japan

[21] Appl. No.: 32,032

[22] Filed: Mar. 30, 1987

Related U.S. Application Data

[63] Continuation of Ser. No. 587,239, Mar. 7, 1984, abandoned.

[30] Foreign Application Priority Data

Mar. 8, 1983 [JP] Japan ................................. 58-38087
Mar. 8, 1983 [JP] Japan ................................. 58-38089

[51] Int. Cl.$^5$ .......................... C12N 15/00; C12N 1/20
[52] U.S. Cl. ............................. 435/252.8; 435/172.3; 435/320; 435/207; 935/73; 935/48
[58] Field of Search .................. 435/172.3, 253, 320, 435/91, 207, 252.8; 536/27; 935/14, 29, 38, 48, 56, 60, 73

[56] References Cited

U.S. PATENT DOCUMENTS

4,411,994 10/1983 Gilbert et al. .................... 435/71

OTHER PUBLICATIONS

Imanaka et al., T. Bact, vol. 147 (3) Sep. 1981, pp. 776–786, "Cloning of the Genes for Penicillinase, penP and penI, of *Bacillus licheniformis* in Some Vector Plasmids and Their Expression in *Escherichia coli, Bacillus subtilis,* and *Bacillus licheniformis*".

Gray et al., T Bact, vol. 145 (1) Jan. 1981, pp. 422–428, "Molecular Cloning and Expression of *Bacillus licheniformis* β-Lactamase Gene in *Escherichia coli* and *Bacillus subtilis*".

Sunaga et al, *Agric Biol Chem.* vol. 40, pp. 1363–1367, 1976 "Production of Penicillinase by an Alkalophilic Bacillus".

*Primary Examiner*—Robin L. Teskin
*Attorney, Agent, or Firm*—Bucknam & Archer

[57] ABSTRACT

A novel plasmid pEAP2, which was constructed from *Bacillus* sp. 170 chromosomal DNA carrying the gene for extracellular production of penicillinase and a vector plasmid pMB9. A novel microorganism, *Escherichia coli* HB101(pEAP2) carrying the plasmid pEAP2 and being capable of extracellular production of penicillinase. The method for cultivation of the microorganism is characterized by culturing it in the medium containing NaCl (or KCl) for 16–48 hours. According to this invention, useful high-molecular substances can be produced in a high yield.

2 Claims, 4 Drawing Sheets

——— : pMB9 PLASMID DNA

▩▩▩▩ : BACILLUS NO. 170 DNA FRAGMENT
　　　　[PENICILLINASE DNA (Pen⁺) FRAGMENT]

PLASMID, METHOD FOR CONSTRUCTION OF THE SAME, MICROORGANISMS CARRYING THE PLASMID AND METHOD FOR CULTIVATION OF THE MICROORGANISM

This is a continuation of application Ser. No. 587,239 filed Nov. 7, 1984 now abandoned.

BACKGROUND OF THE INVENTION (1) Field of the Invention

This invention relates to a novel plasmid, a method for construction of the plasmid, a novel microorganism carrying the plasmid, and a method for cultivation of the microorganism and relates more particularly to a novel plasmid with DNA coding for extracellular production of such high-molecular substances as penicillinase, a novel microorganism transformed with the plasmid, and a method for extracellular production of such high-molecular substances as penicillinase by culturing the microorganism.

(2) Description of the Prior Art

Plasmid is a non-chromosomal gene of cyclic DNA found in a microorganism cell. Plasmid is currently being used as a means for recombination of microorganism gene and it is becoming more and more important in the field of fermentation industry.

Studies have recently been done on plasmids carrying foreign DNA having genetic information of metabolic products or specific demand for growth of microorganism, as shown in production of amino acids or peptides. Some plasmids have been introduced into host microorganisms to obtain transformants. Methods have been proposed for producing relatively low molecular compounds such as amino acids and peptides by culturing the transformants. However, the degree of propagation of plasmids carrying genes for production of high-molecular substances depends on the nature of host microorganisms and those plasmids have not effectively been expressed. Furthermore, no effective methods for cultivation of such transformants have been established.

It has not been possible to selectively obtain a certain extracellular high-molecular product by culturing a microorganism transformed with a plasmid carrying foreign DNA fragment having genetic information of extracellular production of high-molecular substances which are metabolic products of another microorganisms. Such extracellular production has not successfully been done even when a transformant of *Escherichia* species, which is usually used as a host microorganism, is used.

USP 4,411,994 of W. Gilbert et al discloses a process for producing specific proteins in bacteria and having them excreted from the bacterial cell. This process comprises inserting the DNA representing the desired non-bacterial protein or part of a protein by recombinant techniques into a plasmid or phage gene for either a periplasmic or an extracellular protein, hereinafter called a "carrier protein", transforming a bacterial host with the recombinant gene, and culturing the transformed host to excrete the protein. The process of this patent provides a means for producing a selected protein by employing a gene for a carrier protein which has a leader sequence of hydrophobic amino acids at its amino terminus.

Cell wall of *Escherichia coli* which has often been used for production of useful physiologically active substances, consists of three kinds of membrane: inner membrane, peptide glycan and outer membrane. The space between the inner and outer membrane is called the periplasmic space. The process of USP4,411,994 has succeeded in the excretion of the products within the periplasmic space but not within the culture medium through the outer membrane or outside the bacterial host cell. In the present invention, by inserting the DNA having genetic information of extracellular production of high-molecular substances into the plasmid to obtain a hybrid plasmid and culturing the host transformed with the hybrid plasmid, it is possible to excrete useful physiologically active substances through the outer membrane and recover them directly from the culture medium. Thus, the present invention makes mass production of useful physiologically active substances possible, which has never been possible by the prior art process.

SUMMARY OF THE INVENTION

Therefore, an object of the present invention is to provide a novel plasmid with DNA carrying genetic information of extracellular production of high-molecular compound, a method for construction of the plasmid, a novel microorganism carrying the plasmid and a method for culturing the microorganism.

A novel plasmid according to the present invention is one which provides a host with extracellular producibility of high-molecular substances such as penicillinase and, which is constructed from a vector plasmid and a DNA fragment having genetic information of extracellular production of high-molecular substances such as penicillinase and being obtained from a microorganism of the genus *Bacillus*.

The plasmid can be prepared by a process which comprises preparing, with a restriction enzyme, a chromosomal DNA fragment coding for extracellular production of penicillinase, digesting a plasmid vector DNA with a restriction enzyme which does not interfere with the genetic information carried on the chromosomal DNA fragment, treating the chromosonal DNA fragment and the digested vector plasmid with DNA ligase to form a recombinant plasmid and isolating the recombinant plasmid.

A novel microorganism according to the present invention is one which belongs to the genus *Escherichia*, which contains the recombinant plasmid and which has extracellular producibility of high-molecular substances such as penicillinase.

The present invention also provides a method for culturing the microorganism thus prepared to produce the high-molecular substances outside the bacterial cell, which comprises inoculating the microorganism in a culture medium containing an inorganic salt necessary for the microorganism to grow, keeping on culturing the microorganism, after the concentration of the microorganism cells reached the maximum and until the production and accumulation of the high-molecular substances in the medium reach the maximum.

DETAILED DESCRIPTION OF THE INVENTION

The term "high molecular substances" used in the specification and the claims of this application means useful physiologically active compounds including bacterial metabolic products such as enzyme proteins, antibiotics and the like, and biologically active proteins of mammalian origin.

The present invention will now be explained in detail.

(a) Plasmid and Construction of the same

A novel plasmid of the present invention is one which is constructed by inserting a foreign DNA or an exogenote into a plasmid (extrachromosomal DNA or vector DNA), such as Col $E_1$, found in *Escherichia coli* cells.

Vector DNA which can be used in the present invention includes those isolated from natural sources, or those from which the DNA fragment unnecessary for self-reproduction has been deleted, such systems as ColE$_1$, pMB9, pBR322, pSC101, R6K and lambda phage.

Foreign DNA fragments or exogenotes which can be inserted into the vector DNA are the genes having genetic information of extracellular production or secretion of high-molecular substances, such as penicillinase, alkalinephosphatase, β-galactosidase.

Exogenotes or DNA fragments which can be used in the present invention include the genes having genetic information of extracellular production or secretion of high molecular substances and being obtained from a microorganism which belongs to, for example, the genus *Bacillus*.

One example of the microorganisms containing the DNA which has genetic information of extracellar penicillinase production and which can be used in the present invention is *Bacillus* sp. No. 170 (Horikoshi K. et al (1976) Agric. Biol. Chem., 40 1363–1367).

For the purpose of the insertion of a foreign DNA into a vector DNA, any conventional methods can be used in the present invention. For instance, a chromosomal DNA is digested with a suitable restriction enzyme or endonuclease to obtain a foreign DNA fragment or an exogenote which is then mixed with a vector DNA which has been treated with the similar restriction enzyme, and the mixture is ligated by a suitable ligase. Thus, as described before, the novel plasmid of the present invention can be obtained by preparing, with a restriction enzyme, a DNA fragment coding for extracellular production of penicillinase, digesting a plasmid vector DNA with a restriction enzyme which does not interfere with genetic information carried on the DNA fragment, treating the DNA fragment and the digested vector plasmid with DNA ligase to construct a recombinant plasmid and isolating the recombinant plasmid in the conventional manner.

Figure 4:
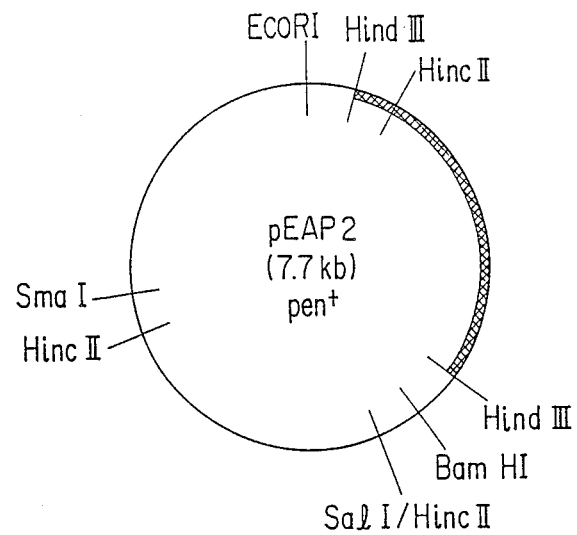
FIG. 4 shows the restriction enzyme cleavage map for the plasmid, pEAP2.

Novel plasmid pEAP2 can be constructed from *Bacillus* sp. No. 170 chromosomal DNA fragment and plasmid pMB9. Restriction enzyme map for plasmid pEAP2 is shown in FIG. 4. As seen from FIG. 4, plasmid pEAP2 is constructed from plasmid pMB9 into which the *Bacillus* sp. No. 170 chromosomal DNA coding for extracellular penicillinase production is inserted between the Hind III restricted site of plasmid pMB9. Thus, plasmid pEAP2 is a cyclic DNA molecule of about 7700 nucleotide base pairs (7.7 kb), consisting of pMB9 DNA and the chromosomal DNA of about 2000 nucletide base pairs (2 kb).

(b) Preparation of Microorganism

The recombinant plasmid constructed from the chromosomal DNA fragment and the vector DNA plasmid is introduced into a host microorganism of the genus Escherichia by a conventional transformation technique. Cultivation is kept on until stabilized genotype is established, to obtain a transformant carrying both genotypes on the selected chromosomal DNA and on the vector DNA. For this purpose, a conventional, so called shot gun method can be used.

Typical host microorganism which can be used in the present invention is *Escherichia coli* HB101 which is a hybrid strain of *Escherichia coli* K-12 and *Escherichia coli* B.

The transformant, *Escherichia coli* HB101 (pEAP2) which is prepared by introducing plasmid pEAP2 into *Escherichia coli* HB 101 has the same microbiological properties as those of the host, *Escherichia coli* HB101, except penicillin resistance [Molecular Cloning, A Laboratory Manual, p.504 (1982), Genotype: $F^-$, hsd S $20(r^-{}_B, m^-{}_B)$, rec A13, ara-14, proA2, lacY1, galK2, rpsL20(Sm'), xyl−5, mtl−1, supE44λ$^-$]. *E. Coli* HB101 (pEAP2) is further characterized by the property of plasmid pEAP2, that is, the extracellular penicillinase producibility.

The extracellular production of penicillinase by *Escherichia coli* HB101 (pEAP2), as shown in Examples described after, reaches more than 80% of total production including the intracellular production and remains after long cultivation. In contrast, more than 80% of the total penicillinase production by the known strain, *Escherichia coli* HB101 (pBR322) is of intracellular and, the extracellular penicillinase production by the known strain, *Bacillus* sp. No. 170 can not be kept for a long period of time.

The present invention which provides *Escherichia coli* HB 101 (pEAP2) having extracellular producibility of enzyme proteins such as penicillinase is not only novel but also inventive. *Escherichia coli* HB101 (pEAP2) can produce and secrete into the medium from the cells, in addition to large amounts of penicillinase, large amounts of other enzyme proteins which can also be collected. More specifically, it has been discovered that *Escherichia coli* HB101 (pEAP2) produces and secretes into the medium from the cells large amounts of alkaline phosphatase, β-galactosidase and about ten kinds of proteins which have been observed only within the cells and never outside the cells.

Such extracellular production by *Escherichia coli* HB101 (pEAP2) demonstrates that the DNA of about 2000 nucleotide base pairs carried on plasmid pEAP2 provides the host with the extracellular producibility of the metabolic products.

(c) Cultivation of the microorganism

For culturing the transformant prepared in step (b), any culture media can be used which are suitable for the production of specific substances for which specific genetic information codes and which are suitable for growth of the microorganisms of the genus *Escherichia*. In the process of the present invention, it is necessary to culture the microorganism in a culture medium containing an inorganic salt necessary for the microorganism to grow, and to keep culturing the microorganism, after the concentration of the microorganism cells reached the maximum, and until the production and accumulation of the high-molecular substances in the medium reach the maximum.

Examples of the inorganic salt which can be used in the present invention include sodium and potassium salts such as sodium chloride, sodium sulfate, potassium chloride and the like, among which sodium chloride is preferred. The media containing the inorganic salt can contain such carbon source as glucose, sucrose, lactose, maltose, glycerol, and the like, such nitrogen source as ammonia water, ammonium salts and the like, inorganic ions and optionally such nutrient as amino acids, vitamin and the like. The culture media which can be used in the present invention are those which use, as a basic medium, LB-broth (containing tryptone, yeast extract and NaCl), BPB-broth (Difco Laboratories; containing polypeptone, yeast extract and $K_2HPO_4$), nutrient broth (Difco 0001), tryptone-NaCl broth or the like Since more than 80% of total products remain in the intracellular fraction in a medium containing no inorganic salt, it is necessary to use a medium containing an inorganic salt in order that most products are secreted into the culture medium out of the cells. The amount of inorganic salt used is in the range of 0.5-3.0% by weight on the basis of the culture medium.

In the culture of *Escherichia coli* HB101 (pEAP2), excellent results are obtained when using the LB-broth to which glucose and further glycerol have been added as carbon sources, preferably in the amount of 0.1 and 0.2% by weight on the basis of the culture medium, respectively.

Although culture conditions such as pH, temperature, oxygen supply or the like can be changed for the optimum growth of the microorganism of the genus *Escherichia*, it is necessary, in the present invention, to keep culturing the microorganism, after the concentration of the microorganism cells reached the maximum, that is to say, after the latter logarithmic phase and until the production and accumulation of the high-molecular substances in the medium reach the maximum.

After the inoculation of the microorganism of the genus *Escherichia* in the medium, the cell concentration reaches the maximum for 5 to 20 hours and the production and accumulation of the high-molecular substances reach the maximum for 16 to 48 hours. Although the pH of the culture mudium is not critical, it is preferred that it be in the range of pH5–pH8, especially pH7. Thus, without further addition of inorganic salt necessary for the microorganism to grow, carbon sources and the like during cultivation, the microorganism produces large amounts of extracellular high-molecular substances which can conveniently be collected.

According to the culture method of the present invention, in addition to enzyme proteins, such high-molecular fermentation products as antibiotics, polysaccharides can be produced in a significant amount. This method can be applied to the cultivation of any microorganisms transformed with a plasmid carrying a foreign DNA coding for biologically active high-molecular substances such as hormone peptide (e.g. insulin) or interferon and the DNA coding for extracellular production or secretion of biologically active high-molecular substances, which leads to mass production of the high-molecular substances such as insulin, interferon and the like.

As explained above, the present invention contributes to the industrial production of useful high-molecular substances.

Examples of microorganisms which may be used in this invention include (i) *Bacillus* sp. No. 170, and (ii) *Escherichia coli* HB101 (pEAP2), all of which were deposited with the Fermentation Research Institute, Agency of Industrial Science and Technology, Ministry of International Trade and Industry, Japan, International Depository Authority (hereinafter referred to as "FERM") under the following accession numbers, respectively, FERM BP-467 and FERM BP-468, and are on deposit with FERM in an unrestricted deposit permitting the full access to the culture.

The depository and accession numbers of the above mentioned microorganisms are shown below:

|      | Microorganisms              | Depository | Accession No. |
| ---- | --------------------------- | ---------- | ------------- |
| (i)  | Bacillus sp. No. 170        | FERM       | FERM BP-467   |
| (ii) | *Escherichia coli* HB101 (pEAP2) | FERM       | FERM BP-468   |

The applicant will maintain the deposition of FERM BP-467 and FERM BP-468 in the unrestricted form until the end of the duration of a patent granted on this application if a patent is granted on this application, and thus said microorganism strains will be available to any third party at any time until the end of the duration of the patent granted on this application.

We will now explain, with reference to Examples, method for construction of the plasmid of the present invention, method for preparation of the transformant, *Escherichia coli* HB101 (pEAP2) and the extracellular production of penicillinase and so on by the transformant.

EXAMPLE 1

(1) Preparation of a chromosomal DNA having genetic information of penicilinase producibility.

Alkalophilic *Bacillus* sp. No. 170 (FERM BP-467) having extracellular producibility of penicillinase was cultured at 30° C. with shaking for 19 hours in the broth (containing 2.0 g of glycerol, 5.0 g of yeast extract, 5.0 g of polypeptone, 1.0 g of $K_2HPO_4$, 0.2 g of $MgSO_4.7H_2O$, 10 g of $NaHCO_3$ in one liter of deionized water; pH9.0). The cells in the latter logarithmic phase were collected, from which a chromosomal DNA was extracted by the phenol extraction method and purified to obtain 5 mg of the chromosomal DNA.

(2) Insertion of chromosomal DNA fragment into vector DNA.

The chromosomal DNA (10 μg) obtained in step (1) was digested with the restriction enzyme Hind III at 37° C. for 5, 10, 20, 30 and 60 minutes to obtain DNA fragments.

Plasmid pMB9 [Bethesda Research Laboratories, U.S.A., tetracycline resistant ($Tet^r$)] used as the vector was cut with Hind III, heated at 65° C. for 5 minutes, and then mixed with the DNA fragments. The mixture was treated with T4 phage DNA ligase at 10° C. for 24 hours and then heated at 65° C. for 5 minutes.

Two times volume of ethanol was added to the mixture. Plasmids carrying the chromosomal DNA fragments were precipitated and collected.

(3) Transformation of the microorganism with plasmids having gene for extracellular production of penicillinase.

Escherichia coli HB101 which is a hybrid strain of Escherichia coli K-12 and Escherichia coli B, was inoculated in 10 ml of LB-broth [containing 10 g of tryptone (Difco Laboratories, Detroit, Mich.), 5 g of yeast extract, 1 g of glucose and 10 g of NaCl in one liter of deionized water; pH was adjusted to 7.0] and cultured at 37° C. with shaking until the latter logarithmic phase. The cells were collected and suspended in an ice-cold $CaCl_2$ solution of 0.03M (final concentration) to obtain competent cells. The cell suspension and the plasmid solution obtained in step (2) were combined and kept on ice for 60 minutes. The mixture was heated to 42° C. for 1 to 2 minutes to introduce the plasmid DNA into the cells. This cell suspension was inoculated in fresh LB-broth and cultured at 37° C. for 3 to 5 hours with shaking. The cells were collected and washed to obtain Escherichia coli HB101 (pEAP2) having penicillinase producibility.

EXAMPLE 2

Preparation and purification of plasmid pEAP2

1. Culture growth of bacterial cells using Escherichia coli HB101 (pEAP2) [FERM BP-468]
   Preculture in LB.  Over night at 37° C.
   ↓
   Culture in M-9.  Add chloramphenicol after 130 Klett units. 16 hr at 37° C.
   ↓
   Centrifugation.  5000 rpm, 20 min at 4° C.
   ↓
   Cell pellets.  Stored at −80° C.

2. Purification of plasmid DNA.
   Cell pellets
   | 10 ml 20% Sucrose, 50 mMTris, 1 mMEDTA PH8.
   | Suspended, Keep on ice.
   ↓
   50 ml polypropylene centrifuge tube.
   | 2 ml, 0.25 M EDTA.
   | 1 ml, Lysozyme (5 mg/ml of 0.025 M Tris, PH8.)
   | 0.1 ml, RNases (10 mg/ml)
   ↓
   Cell lysis. Mix gently. Stand 15 to 30 min on ice.
   | 5 ml, 3× Triton. Mix gently.
   | Stand 15 to 45 min on ice.
   ↓
   Centrifugation. 17,000 rpm, 40 min at 4° C.
   ↓
   Supernatant soln in plastic cylinder.
   ↓
   250 ml glass bottle.
   | ⅔ vol DD $H_2O$
   | ⅔ vol Cold saturated phenol. Mix gently
   ↓
   Centrifugation. 6500 rpm, 15 min at 4° C.
   ↓
   Upper phase.
   | Equal vol. of phenol; Chloroform.
   ↓
   Centrifugation. 6500 rpm, 15 min at 4° C.
   ↓
   Upper phase in 250 ml bottle.
   | 1/25 vol 5 M NaCl.
   | 2 vol EtOH at −20° C.
   | Over night at −20° C.
   ↓
   Centrifugation. 6500 rpm, 60 min at −20° C.
   ↓
   DNA pellet. Dry excess liquid.
   | 5 ml A-50 buffer, resuspended.
   | 1 ml sterile 80% glycerol, mix gentry.
   ↓
   A-50 column. (2 × 35 cm, lfraction = 4 ml.)
   ↓
   DNA fraction. ($A_{260}$ peak.)
   | 2 vol EtOH at −20° C. Over night at −20° C.
   ↓
   Centrifugation. 6500 rpm, 60 min at −20° C.
   ↓
   DNA pellet.
   | 2.1 ml TEN buffer in 5 ml cellulose nitrate tube.
   | 2.2 g CsCl, mix.
   | (In dark.)
   | 150 ul PdI (2 mg/ml). Mix well.
   | 2 ml mineral oil on top of tube.
   ↓
   CsCl gradient centrifugation. 36,000 rpm, 40 hr at 20° C.
   | Visible with UV.  Upper band; chromosomal & nicked DNA.
   |                   Lower band; covalently closed p-DNA.
   ↓
   Collect of lower band DNA by drop wise.
   ↓
   Dowex 50W-X8 column. UV check.
   | (In light.)
   ↓
   Dialysis against 2 to 4l of 10 mM Tris, 1 mM EDTA PH8.

-continued

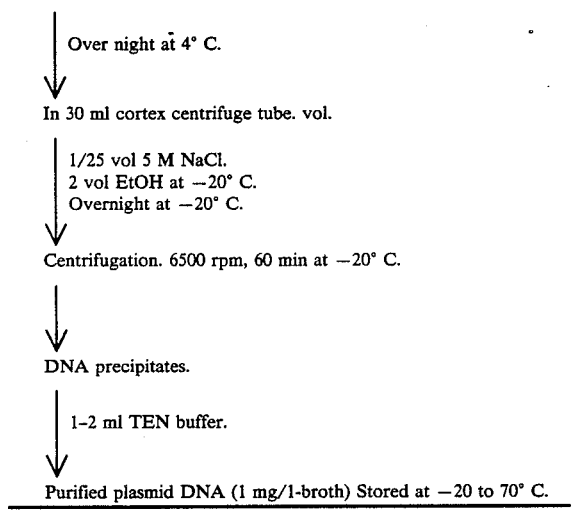

Over night at 4° C.
↓
In 30 ml cortex centrifuge tube. vol.
  1/25 vol 5 M NaCl.
  2 vol EtOH at −20° C.
  Overnight at −20° C.
↓
Centrifugation. 6500 rpm, 60 min at −20° C.
↓
DNA precipitates.
  1–2 ml TEN buffer.
↓
Purified plasmid DNA (1 mg/1-broth) Stored at −20 to 70° C.

EXAMPLE 3

*Escherichia coli* HB101 (pEAP2) (FERM BP-468) obtained in step (3) of Example 1 was inoculated in 500ml-flasks containing 100 ml of LB-broth (containing 10 g of tryptone, 5 g of yeast extract, 1 g of glucose, 2 g of glycerol, and 10 g of NaCl in one liter of water) and cultured at 37° C. with shaking. Cell growth (cell amount) was measured by optical density at 660nm.

Extracellular and intracellular penicillinase activities were assayed by the modified Sargent's method [Sawai et al; Antimicrob. Agents Chemother. 13, 910 (1978)], wherein enzyme quantity hydrolysing at 30° C. one micro mole of benzylpenicillin per one minute constitutes one unit of penicillinase.

Figure 2:
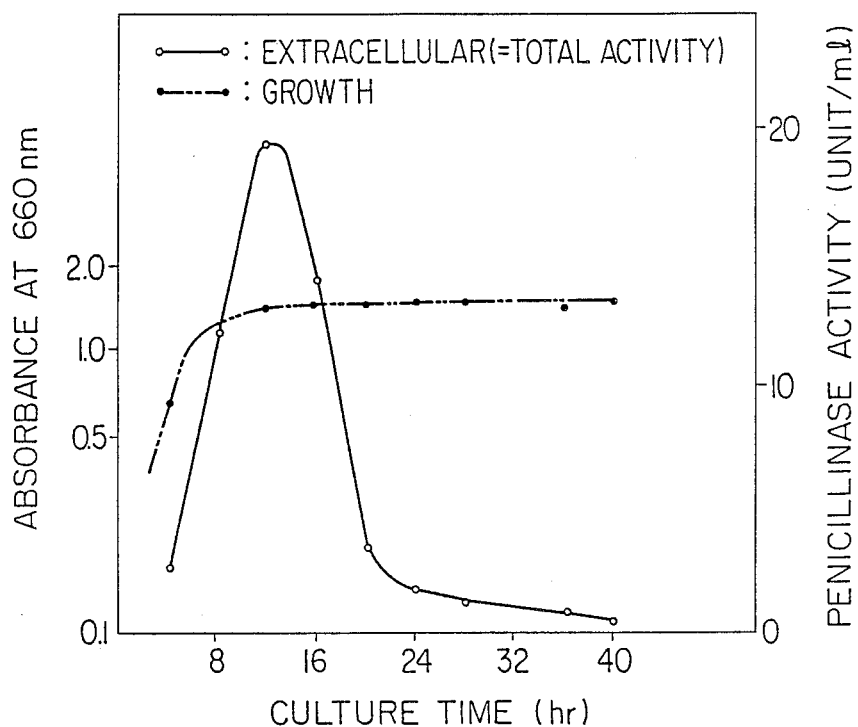
FIG. 2 shows bacterial growth and penicillinase production by *Bacillus* sp. No. 170.

As shown in FIG. 2, cell growth of the transformant reached the maximum after 16 hours cultivation and extracelluar penicillinase activity began to increase after 20 hours and reached the maximum (about 20 units/ml) after 28 hours cultivation.

Figure 1A:
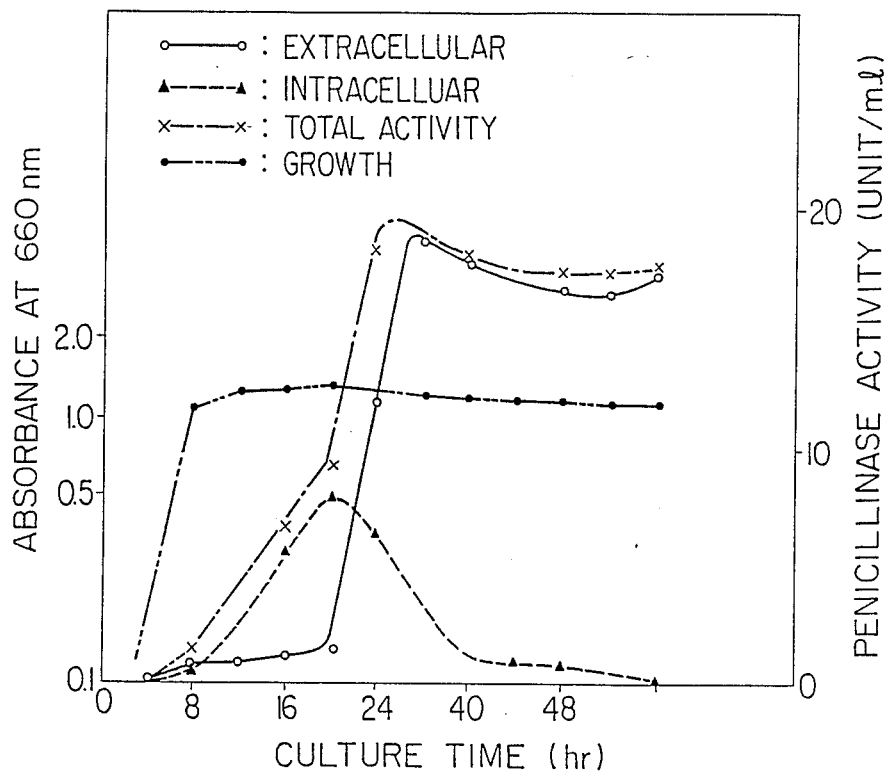
FIG. 1a shows bacterial growth and penicillinase production by *Escherichia coli* HB101(pEAP2) of the present invention.
Figure 1B:
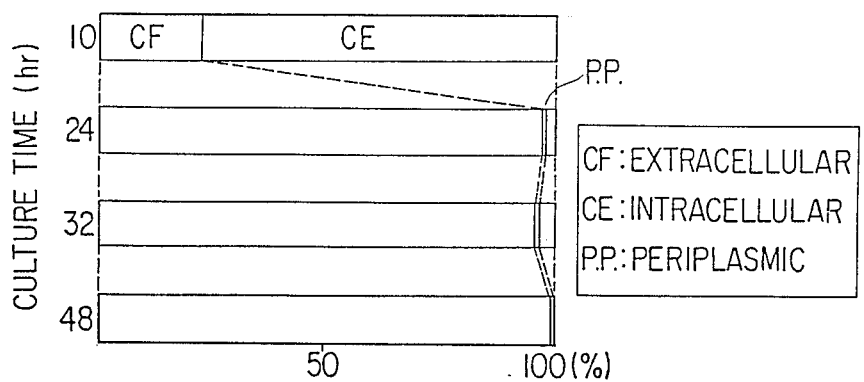
FIG. 1b shows percentages of extracellular, intracellular, and periplasmic cellular penicillinase production by *Escherichia coli* HB101(pEAP2).

The extracellular penicillinase produced was very stable and, as shown in FIG. 1a, the production was kept high even after 48 hours cultivation and reached more than 80% of total enzyme production. In contrast, intracellular penicillinase production was detected at an early phase (after 8 to 20 hours cultivation). But, the maximum was only 8 units/ml or about 10% of total enzyme production and furthermore, the intracellular production decreased quickly. No intracellular penicillinase activity was observed after 48 hours cultivation. FIG. 1b shows percentages of extracellular and intracellular penicillinase activities on total enzyme activity. As a comparison, *Bacillus* sp. No. 170 (FERM BP-467) which is a DNA donor and *Escherichia coli* HB101 (pBR322) (carrying plasmid pBR322 having genetic information of penicillinase production) [Boyer et al; Gene, vol. 2, p.95–113 (1977)] were cultured and penicillinase activities were assayed.

Bacillus sp. No. 170 was inoculated in 500ml-flasks containing 100 ml of the broth (containing 2.0 g of glucose or glycerol, 5.0 g of yeast extract, 5.0 g of polypeptone, 1.0 g of $K_2HPO_4$, 0.2 g of $MgSO_4.7H_2O$ and 10 g of $NaHCO_3$ in one liter of water and adjusted to pH 9.0) and cultured at 37° C. with shaking. Extracellular penicillinase activity in the culture fluid was observed every four hours. It reached the maximum (19 units/ml) after 12 hours cultivation and then quickly decreased. No extracellular penicillinase activity was observed after 40 hours cultivation (FIG. 2).

Figure 3A:
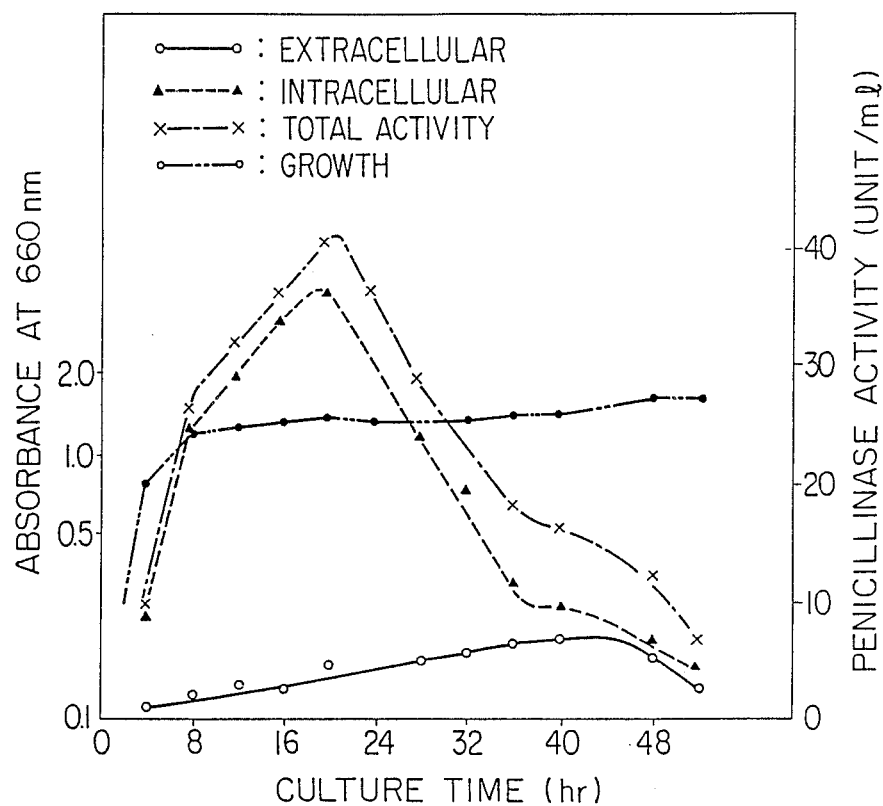
FIG. 3a shows bacterial growth and penicillinase production by *Escherichia coli* HB101(pBR322).
Figure 3B:
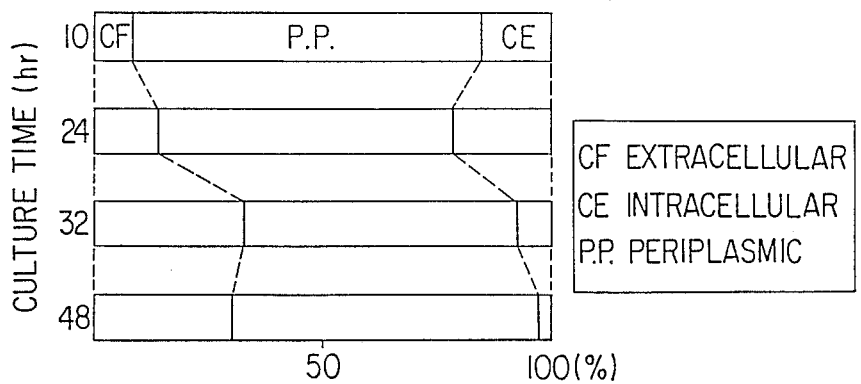
FIG. 3b shows percentages of extracellular, intracellular, and periplasmic cellular penicillinase production by *Escherichia coli* HB101(pBR322).

On the other hand, *Escherichia coli* HB101 (pBR322) was inoculated in 500ml-flasks containing 100 ml of LB-broth which is the same as that used in the cultivation of *Escherichia coli* HB101 (pEAP2) and cultured at 37° C. with shaking. As shown in FIG. 3a, intracellular penicillinase activity reached the maximum (35 units/ml) after 20 hours cultivation and it was more than 80% of total enzyme activity. But it decreased quickly. Extracellular penicillinase activity was less than 10% of total enzyme activity. FIG. 3b shows percentages of extracellular and intracellular penicillinase activities on total enzyme activity.

[Identification of Penicillinase]

The culture fluid of the transformant obtained in step (3) of Example 1 was centrifuged at $10,000 \times g$ for 10 minutes. The supernatant fluid was brought to 80% saturation with ammonium sulfate. The precipitate was dissolved in water and the solution was dialyzed overnight against 0.05M phosphate buffer containing 0.1M NaCl (pH 7.0). The dialysate was applied on a Sephadex G-75 column equilibrated with the phosphate buffer to obtain purified penicillinase.

Similarly, the culture fluid of *Bacillus* sp. No. 170 was treated to obtain purified penicillinase.

For the identification of *Escherichia coli* HB101 (pEAP2) penicillinase with *Bacillus* sp. No. 170 penicillinase, effects of pH on activity, thermal stability and molecular weight of each penicillinase were investigated. As a result, the enzymes were identical with each other as shown below.

(a) Stability of the enzyme was investigated in buffer solutions of various pH values. The mixture was incubated at 30° C. for 45 minutes.

Both the enzymes were stable between pH 7 and pH 9 and the optimum pH values for enzyme action were 6.0 to 7.0.

(b) Thermal stability was investigated as follows The enzymes were dissolved in 0.05M phosphate buffer of pH 7.0 and the solutions were heated at the selected temperature for 10 minutes. The residual activities were measured at pH 7.0. Both the enzymes were stable up to 50° C.

(c) Estimation of molecular weight of the enzymes was done by using the Sephadex gel filtration method. Estimated molecular weight of both the enzymes was 27,000 to 22,000.

EXAMPLE 4

Culture conditions for penicillinase production by *Escherichia coli* HB101 (pEAP2)(FERM BP-468) were examined in the various media. The other culture conditions were the same as those in Example 3.

TABLE 1

| Media | Time (hrs.) | Penicillinase Activity (U/ml) | | |
|---|---|---|---|---|
| | | Extracellular | Intracellular | Total |
| LB-broth | 20 | 14.7 (88.5%) | 1.9 (11.5%) | 16.6 |
| | 30 | 15.6 (84.8%) | 2.8 (15.2%) | 18.4 |
| BPB-broth | 20 | 1.6 (10%) | 14.6 (90%) | 16.2 |
| | 30 | 9.1 | 14.2 | 23.3 |

TABLE 1-continued

| Media | Time (hrs.) | Penicillinase Activity (U/ml) | | |
|---|---|---|---|---|
| | | Extracellular | Intracellular | Total |
| | | (39%) | (61%) | |

Effects of components of LB-broth on penicillinase production are given in Table 2. The concentration of tryptone, tryptose, polypeptone and NaCl was 1% by weight.

TABLE 2

| Component | Time (hrs.) | Penicillinase Activity (U/ml) | | |
|---|---|---|---|---|
| | | Extracellular | Intracellular | Total |
| Tryptone NaCl | 20 | 14.7 (88.5%) | 1.9 (11.5%) | 16.6 |
| | 30 | 15.6 (84.8%) | 2.8 (15.2%) | 18.4 |
| Tryptone | 20 | 2.2 (20%) | 8.8 (80%) | 11.0 |
| | 30 | 3.1 (28.7%) | 7.7 (71.3%) | 10.8 |
| Tryptose NaCl | 20 | 13.7 (92.5%) | 1.1 (7.5%) | 14.8 |
| | 30 | 15.4 (90.5%) | 1.6 (9.5%) | 17.0 |
| Trytose | 20 | 1.4 (15.7%) | 7.5 (84.3%) | 8.9 |
| | 30 | 2.3 (20.9%) | 8.7 (79.1%) | 11.0 |
| Polypeptone NaCl | 20 | 16.4 (91.6%) | 1.5 (8.4%) | 17.9 |
| | 30 | 17.1 (95.5%) | 0.7 (4.5%) | 17.8 |
| Polypeptone | 20 | 1.8 (24%) | 5.7 (76%) | 7.5 |
| | 30 | 3.4 (36.9%) | 5.8 (63.1%) | 9.2 |

Effects of carbon sources of LB-broth on penicillinase production are given in Table 3. The concentration of glucose, starch, sucrose and maltose was 0.1%, that of glycerol was 0.2% and that of NaCl was 1%.

TABLE 3

| Carbon source | Time (hrs.) | Penicillinase Activity (U/ml) | | |
|---|---|---|---|---|
| | | Extracellular | Intracellular | Total |
| Glucose NaCl | 20 | 17.3 (94.0%) | 1.1 (6%) | 18.4 |
| | 30 | 15.1 (96.7%) | 0.5 (3.3%) | 15.6 |
| Glycerol NaCl | 20 | 5.4 (90.0%) | 0.6 (10.0%) | 6.0 |
| | 30 | 5.2 (74.3%) | 1.8 (25.7%) | 7.0 |
| Starch NaCl | 20 | 6.6 (74.2%) | 2.3 (25.8%) | 8.9 |
| | 30 | 4.9 (55.7%) | 3.9 (44.3%) | 8.8 |
| Sucrose NaCl | 20 | 7.1 (78.0%) | 2.0 (22.0%) | 9.1 |
| | 30 | 6.5 (60.2%) | 4.3 (39.8%) | 10.8 |
| Maltose NaCl | 20 | 12.8 (89.3%) | 1.5 (10.7%) | 14.3 |
| | 30 | 11.8 | 2.6 | 14.4 |

TABLE 3-continued

| Carbon source | Time (hrs.) | Penicillinase Activity (U/ml) | | |
|---|---|---|---|---|
| | | Extracellular | Intracellular | Total |
| Glucose Glycerol NaCl | 30 | (81.9%) 20.0 (94.3%) | (18.1%) 1.2 (5.7%) | 21.2 |

Effects of NaCl on penicillinase production were examined using the media containing 1% of tryptone, 0.1% of glucose, 0.2% of glycerol, 1% of yeast extract and the indicated amount of NaCl. Results are given in TAble 4.

TABLE 4

| Nacl (%) | Extracellular activity (U/ml) |
|---|---|
| 0 | 0.2 |
| 0.5 | 15.0 |
| 1.0 | 20.0 |
| 2.0 | 18.0 |
| 5.0 | 8.0 |
| 10.0 | 0.1 |

EXAMPLE 5

Escherichia coli HB101, Escherichia coli HB101 (pMB9) and Escherichia coli HB101 (pEAP2) (FERM BP-468) were cultured in the same LB-broth as used in example 3 at 37° C. for 20 hours with shaking. Enzyme activities of alkaline phosphatase and galactosidase were measured by optical density at 420 nm. Results are given in Table 5.

TABLE 5

| Micro-organism | Products | Activity (U/ml) | | |
|---|---|---|---|---|
| | | Extracellular | Intracellular | Total |
| E. coli HB101 | Proteins* | 0.04 (4%) | 1.04 (96%) | 1.08 (100%) |
| | Alkaline phosphatase | 0.02 (2%) | 1.31 (98%) | 1.33 (100%) |
| | β-Galactosidase | 0.03 (2%) | 1.20 (98%) | 1.23 (100%) |
| E. coli HB101 (pMB9) | Proteins* | 0.01 (1%) | 0.78 (99%) | 0.79 (100%) |
| | Alkaline phosphatase | 0.01 (2%) | 0.47 (98%) | 0.48 (100%) |
| | β-Galactosidase | 0.00 (0%) | 0.80 (100%) | 0.80 (100%) |
| E. coli HB101 (pEAP2) | Proteins* | 0.18 (21%) | 0.67 (79%) | 0.85 (100%) |
| | Alkaline phosphatase | 0.29 (58%) | 0.21 (42%) | 0.50 (100%) |
| | β-Galactosidase | 0.09 (10%) | 0.81 (90%) | 0.90 (100%) |
| | Penicillinase | 10.70 (83%) | 2.20 (17%) | 12.90 (100%) |

*Proteins contain about 10 kinds of proteins and are represented in mg/ml.

We claim:

1. A culture comprising Escherichia coli which has been transformed by plasmid pEAP2 and which secretes more than 80% of penicillinase relative to the total cellular production of penicillinase.

2. The culture of claim 1 wherein the Escherichia coli is HB 101.

* * * * *